US011963540B2

(12) United States Patent
Currie et al.

(10) Patent No.: US 11,963,540 B2
(45) Date of Patent: Apr. 23, 2024

(54) DEVICE AND METHOD FOR PASTEURIZING AND/OR STERILIZING PARTICULATE MATERIAL

(71) Applicant: BÜHLER AG, Uzwil (CH)

(72) Inventors: Alasdair Currie, London (GB); Martin Hersche, Flawil (CH)

(73) Assignee: Bühler AG, Uzwil (CH)

( * ) Notice: Subject to any disclaimer, the term of this patent is extended or adjusted under 35 U.S.C. 154(b) by 814 days.

(21) Appl. No.: 16/970,806

(22) PCT Filed: Feb. 20, 2019

(86) PCT No.: PCT/EP2019/054242
§ 371 (c)(1),
(2) Date: Aug. 18, 2020

(87) PCT Pub. No.: WO2019/162342
PCT Pub. Date: Aug. 29, 2019

(65) Prior Publication Data
US 2021/0022374 A1 Jan. 28, 2021

(30) Foreign Application Priority Data
Feb. 20, 2018 (EP) ..................................... 18157711

(51) Int. Cl.
*A61L 2/08* (2006.01)
*A23B 9/06* (2006.01)
(Continued)

(52) U.S. Cl.
CPC ................ *A23L 3/263* (2013.01); *A23B 9/06* (2013.01); *A23K 30/00* (2016.05); *A61L 2/087* (2013.01);
(Continued)

(58) Field of Classification Search
CPC ........ A61L 2/26; A61L 2/087; A61L 2202/11; A61L 2202/122; A61L 2202/123; A23B 9/06; A23K 30/00; A23L 3/263
See application file for complete search history.

(56) References Cited

U.S. PATENT DOCUMENTS 3,780,308 A * 12/1973 Nablo ................... B67C 7/0073
250/493.1
5,194,742 A * 3/1993 Avnery ..................... G21K 5/10
250/515.1
(Continued)

FOREIGN PATENT DOCUMENTS

DE 10 2012 209 434 A1 12/2013
EP 0 513 135 B1 11/1992
(Continued)

OTHER PUBLICATIONS

Lianzhong D. et al., "A Study on Chemical Composition of Species Irradiated by Electron Beam", Radiation Physics and Chemistry, Jun. 1, 1998, pp. 49-52 (See EP and International Searches).
(Continued)

Primary Examiner — Sean M Luck
(74) Attorney, Agent, or Firm — Finch & Maloney PLLC

(57) ABSTRACT

A device (10) for pasteurizing and/or sterilizing particulate material. The device (10) includes: an outer housing (40); a material inlet (43); a material outlet (44); a material guide channel (41) for guiding the material through the device (10) to the material outlet (44); at least one electron source (20) for generating an electron beam; and a treatment zone (19), located in the material guide channel (41), for pasteurizing and/or sterilizing while the material is free falling. The device (10) has at least one inner shielding section (51, 52) disposed within the outer housing (40) and enclosing the material guide channel (41) for shielding off radiation produced during treatment. A method for pasteurizing and/or
(Continued)

sterilizing particulate material using such a device (10) is also disclosed which includes: a) generating an electron beam, and b) pasteurizing and/or sterilizing the material, while the material is free falling in the treatment zone (19).

19 Claims, 3 Drawing Sheets

(51) Int. Cl.
*A23K 30/00* (2016.01)
*A23L 3/26* (2006.01)
*A61L 2/26* (2006.01)

(52) U.S. Cl.
CPC .............. *A61L 2/26* (2013.01); *A61L 2202/11* (2013.01); *A61L 2202/122* (2013.01); *A61L 2202/123* (2013.01)

(56) References Cited

U.S. PATENT DOCUMENTS

| | | | |
|---|---|---|---|
| 5,801,387 A | 9/1998 | Nablo et al. | |
| 6,486,481 B1* | 11/2002 | Tigera | H01J 33/00 250/435 |
| 6,745,512 B1 | 6/2004 | Panzer et al. | |
| 9,736,977 B2 | 8/2017 | Kotte et al. | |
| 2004/0261620 A1* | 12/2004 | Thompson | A61L 9/20 96/16 |
| 2006/0151714 A1* | 7/2006 | Thilly | B65B 3/003 250/453.11 |
| 2006/0186350 A1* | 8/2006 | Fontcuberta | A61L 2/087 250/492.1 |
| 2006/0284111 A1* | 12/2006 | Naslund | B65B 55/08 250/492.1 |
| 2008/0175752 A1* | 7/2008 | Perot | A61L 2/087 422/186 |
| 2008/0193341 A1* | 8/2008 | Fontcuberta | A61L 2/087 422/186 |
| 2008/0286424 A1* | 11/2008 | Patel | A23C 3/07 426/240 |
| 2009/0148340 A1* | 6/2009 | Hansen | A61L 2/10 250/455.11 |
| 2009/0285362 A1* | 11/2009 | Birnbach | A61L 2/0011 378/122 |
| 2010/0075003 A1* | 3/2010 | Lindsay | A23B 4/015 426/240 |
| 2011/0006225 A1* | 1/2011 | Fletcher | A61L 2/24 53/558 |
| 2012/0100577 A1* | 4/2012 | Medoff | C08H 8/00 435/155 |
| 2013/0252340 A1* | 9/2013 | Haertling | G01N 21/643 436/1 |
| 2014/0209093 A1* | 7/2014 | Medoff | C10G 32/04 127/42 |
| 2015/0071818 A1 | 3/2015 | Scheuren et al. | |
| 2015/0216106 A1 | 8/2015 | Kotte et al. | |
| 2017/0056539 A1 | 3/2017 | Mellbin | |
| 2017/0057679 A1 | 3/2017 | Ogawa et al. | |
| 2019/0183137 A1* | 6/2019 | Meneses | A23B 9/06 |

FOREIGN PATENT DOCUMENTS

| | | |
|---|---|---|
| EP | 0 705 531 B1 | 6/1996 |
| EP | 1 080 623 A1 | 3/2001 |
| EP | 2 371 397 A1 | 10/2011 |
| EP | 2 668 963 A1 | 12/2013 |
| EP | 2 845 609 A1 | 3/2015 |
| JP | S58192206 U | 12/1983 |
| JP | 2001321139 A | 11/2001 |
| JP | 2002333499 A | 11/2002 |
| JP | 2008056282 A | 3/2008 |
| JP | 2011201600 A | 10/2011 |
| JP | 2015212156 A | 11/2015 |
| JP | 2016077433 A | 5/2016 |
| JP | 2017508522 A | 3/2017 |
| WO | 91/11096 A1 | 8/1991 |
| WO | 99/39750 | 8/1999 |
| WO | 03/017747 A1 | 3/2003 |
| WO | 2013/182500 A1 | 12/2013 |
| WO | 2018/036899 A1 | 3/2018 |
| WO | 2018/036900 A1 | 3/2018 |

OTHER PUBLICATIONS

European Search for corresponding EP application No. 18157711.5 dated Aug. 27, 2018.
International Search for corresponding PCT application No. PCT/EP2019/054242 dated Apr. 12, 2019.
Written Opinion for corresponding PCT application No. PCT/EP2019/054242 dated Apr. 12, 2019.
Japanese Office Action for corresponding JP Application No. 2002-543959 dated Nov. 2, 2021.
Chinese Office Application corresponding to 201980014151.3 dated May 18, 2022.

* cited by examiner

DEVICE AND METHOD FOR PASTEURIZING AND/OR STERILIZING PARTICULATE MATERIAL

The present invention relates to apparatuses and processes for pasteurizing and/or sterilizing particulate material by means of an electron beam.

Here and in the following, particulate materials are referred to as materials consisting of grains and/or flakes, whereby the particles can have for example a spherical, plate-like or edged shape. They can also be ground particles. Pasteurization and/or sterilization can, for example, kill or render harmless microorganisms, at least to a large extent. In particular, a reduction of harmful micro-organisms by at least one, preferably at least five, particularly preferably at least seven orders of magnitude can be achieved.

A generic apparatus is known from EP 1 080 623 B1, for example. This apparatus contains vibratory conveyors with which seeds can be singulated into a transparent curtain. This curtain is then passed through an electron field generated by an electron accelerator, which can, for example, cause the seed to be sterilized. A grid is used to keep the seeds away from an exit window of the electron accelerator.

From U.S. Pat. No. 5,801,387 A, another generic apparatus is known. In this invention, a particulate material is metered into a horizontal air stream with a vibratory feeder and then exposed to an electron beam. Subsequently, a vacuum pump and a filter are used to classify the material.

Furthermore, DE 10 2012 209 434 A1 discloses an apparatus which singulates a free-flowing product, with the aid of a vibratory feeder device and a rotating brush roller, and sets it in rotation. The particles then pass an electron field in a free-falling manner.

In EP 0 513 135 B1, an apparatus is disclosed with which seeds are introduced into a vertical fall chute by means of rotary valves, where they are exposed to electron beams in the vertical fall.

From EP 0 705 531 B1, another apparatus is known, which introduces the seed into a process chamber by means of a dosing apparatus not described in detail, where it falls vertically through an electron beam.

Further apparatuses and processes for pasteurizing and/or sterilizing particulate material are disclosed in the applicant's international patent application PCT/EP2017/070842. The apparatuses contain at least one electron source for generating an electron beam and a treatment zone in which the materials can be pasteurized and/or sterilized by means of the electron beam. In a first aspect, the apparatus further includes a first vibration surface which is excitable to vibrations in order to convey and singulate the material, the first vibration surface comprising a plurality of troughs in which the material is conveyable and by means of which it is separable. In a second aspect, the apparatus has a material channel in the region of the treatment zone, in which the material can be pasteurized and/or sterilized by means of the electron beam, the apparatus having at least one secondary channel through which a fluid can flow, which extends at least partially between the electron source and the material channel and is fluid-separated from the material channel. Also disclosed is a cassette for insertion into an apparatus for pasteurizing and/or sterilizing particulate material.

During the treatment of the material in the treatment zone, radiation may be generated which may be harmful to the environment, especially to the operating personnel. In addition, the radiation can also have a negative effect on the material itself as long as it is guided in the apparatus, especially away from the treatment zone.

It is an object of the present invention to overcome the disadvantages known from the prior art. In particular, apparatuses and methods shall be provided which suppress as far as possible the effects of the radiation generated during the treatment of the material. Amongst other things, the material away from the treatment zone and also the surroundings of the apparatus, in particular its operator, should be protected from the radiation as far as possible.

The apparatus according to the invention for pasteurizing and/or sterilizing particulate material comprises an outer housing, a material inlet, a material outlet, a material guide channel in which the material can be guided from the material inlet along a material guide direction through the apparatus to the material outlet, at least one electron source arranged within the housing for generating an electron beam and a treatment zone arranged in the material guide channel in which the material can be pasteurized and/or sterilized, in particular in a free-falling manner, by means of the electron beam. Here, "pasteurization" or "pasteurizing" means in particular a reduction of the bacterial count by log 5, preferably log 6, particularly preferably log 7 or more. Here, "sterilization" or "sterilizing" is understood in particular to mean complete disinfection. The material is described as "freely falling" if the trajectories of the individual particles of the material are determined solely by their velocity, the gravity acting on them and, if necessary, a process gas by which the material is surrounded. In particular, freely falling particles of the material do not slide on a surface through the treatment zone. The process gas may be air, for example. However, it is also conceivable that a gas which prevents ozone formation, such as nitrogen, is used as the process gas.

In accordance with the invention, the apparatus has at least one internal shielding arranged inside the outer housing and enclosing the material guide channel, in particular along the material guide direction, with at least one shielding element for shielding the radiation generated during the treatment.

In the context of the present invention, an internal shielding is understood to be a further shielding arranged within the outer housing, the shielding elements of which belong at most partially or not at all to the outer housing. It is advantageous that the outer housing of the apparatus also forms a shielding for the radiation produced during the treatment.

Due to the internal shielding, the risks due to the radiation generated during treatment are reduced considerably further than would be possible with only the outer housing. This means that the materials can also be protected from the potentially harmful radiation inside the apparatus, i.e. away from the treatment zone. In addition, the surroundings of the apparatus, in particular its operator, can be protected even more effectively against possible risks of radiation.

Preferably, the material guide channel encloses at least one channel section in which the shielding encloses it in a labyrinth-like manner. A labyrinth-like enclosure by the shielding is understood here and in the following to mean that the shielding elements are designed and arranged in such a way that they can prevent a straight-line propagation of the radiation generated in the treatment zone out of the treatment zone into the surroundings of the apparatus, i.e. into the space outside the outer housing of the apparatus. In this way the shielding effect can be further improved.

It is preferable if the material guide channel contains a material inlet channel in which the material can be guided from the material inlet to the treatment zone, whereby at least one inner shielding encloses the material inlet channel in a labyrinth-like manner. A labyrinth-like enclosure is understood as above. This prevents the radiation generated in the treatment zone from hitting the material before it has reached the treatment zone.

It is also preferred if the material guide channel contains a material outlet channel in which the material can be guided from the treatment zone to the material outlet, whereby at least one inner shielding encloses the material outlet channel in a labyrinth-like manner. This prevents the radiation generated in the treatment zone from hitting the material even after it has already left the treatment zone.

With further advantage, the housing has at least one opening which can be closed by means of at least one closing element associated with it, the closing element containing at least one of the shielding elements on an inner side. In a closed position of the closing element, the latter closes the opening associated with it. The closing element can be a door, for example. This makes it possible that, in the closed position of the closure element, the risk of radiation escaping from the apparatus is reduced even in the area of the opening. When the closure element is open, many of the components of the apparatus are accessible. For example, a cassette, described below, which holds a protective foil between the electron source and the treatment zone, may be easily accessible. This simplified accessibility makes it easier to clean and replace the protective film if necessary.

It is useful if the shielding contains a static first shielding element and the shielding element of the closure element forms a second shielding element, whereby the first shielding element and the second shielding element together enclose the material guide channel, in particular in a labyrinth-like manner, in the closed position of the closure element.

The shielding elements may contain or consist of lead, for example. In a preferred embodiment, the shielding elements have a multi-layer structure with at least one inner layer of lead and two outer layers of another material. The outer layers should preferably be made of a material which may come into contact with the treated materials, especially a foodstuff. For example, the outer layers may be made of stainless steel or a plastic material.

Furthermore, it is advantageous if the material guide channel is limited by wall elements of which at least one and preferably all are connected or connectable to the housing in a movable or even detachable manner, directly or indirectly. This simplifies the replacement of the detachable wall elements, for example if they are defective or have to be cleaned or if different wall elements are required for different materials treated with the apparatus. The wall elements of the material guide channel also include the optional closing elements, vibration surfaces, sliding surfaces and protective foils described below.

The at least one electron source may be known per se. The apparatus may contain one or more electron sources. If there are several electron sources, they may be arranged opposite one another or one after the other with respect to the direction of flow of the material.

Furthermore, it is also conceivable and is within the scope of the invention that the apparatus has several treatment zones. In this way an even more effective pasteurization and/or sterilization can be achieved. Alternatively, the material can be passed several times through one and the same treatment zone.

The apparatus may also have one or more of the features disclosed by the applicant in the aforementioned international patent application PCT/EP2017/070842:

I. Apparatus for pasteurizing and/or sterilizing particulate material, comprising a first vibration surface, which is preferably aligned essentially horizontally and can be excited to vibrate in order to convey and singulate the material, at least one electron source for generating an electron beam, a treatment zone arranged downstream of the first vibration surface, in which the material can be pasteurized and/or sterilized, in particular in a free-falling manner, by means of the electron beam, wherein the first vibration surface comprises a plurality of channels in which the material can be conveyed and by means of which it can be singulated.

II. Apparatus according to feature combination I, wherein the apparatus has, downstream of the first vibration surface and upstream of the treatment zone, an inclined sliding surface which is constructed and arranged such that the material thereon can slide towards the treatment zone.

III. Apparatus according to feature combination II, wherein the sliding surface comprises at least one channel, preferably a plurality of channels, which is/are formed and arranged in such a way that the material can slide and be singulated therein.

IV. Apparatus according to one of the features feature combinations II and III, wherein the sliding surface is inclined downwards with respect to a horizontal at an angle which is in the range from 45° to 85°, preferably 55° to 75°, particularly preferably 60° to 70°.

V. Apparatus according to one of the preceding feature combinations, wherein the apparatus has a deflection surface downstream of the first vibration surface and upstream of the treatment zone, in particular upstream of the sliding surface, which is constructed and arranged in such a way that the material is deflected thereon and can slide from the first vibration surface to the sliding surface and/or in the direction of the treatment zone.

VI. Apparatus according to feature combination V, wherein the deflecting surface comprises at least one channel, preferably a plurality of channels, which is/are constructed and arranged in such a way that the material can slide therein.

VII. Apparatus according to one of the preceding feature combinations, wherein the apparatus has a substantially flat and preferably substantially horizontally oriented second vibration surface upstream of the first vibration surface, which is excitable to vibrations.

VIII. Apparatus for pasteurizing and/or sterilizing particulate material, comprising at least one electron source for generating an electron beam, a treatment zone in which the material can be pasteurized and/or sterilized, in particular in a free-falling manner, by means of the electron beam, in particular apparatus according to one of the preceding feature combinations, wherein the apparatus has a material channel in the region of the treatment zone, in which the material can be pasteurized and/or sterilized by means of the electron beam, the apparatus having at least one secondary channel through which a fluid can flow, which extends at least partially between the electron source and the material channel and is fluid-separated from the material channel.

IX. Apparatus according to feature combination XIII, wherein a protective film which is at least partially permeable to the electron beam and in particular consists of a metal, preferably titanium, is arranged between the electron source and the material channel.

X. Apparatus according to feature combination IX, whereby the protective film separates the material channel from the secondary channel.

XI. Apparatus according to one of the feature combinations IX and X,
wherein the secondary channel is at least partially located between the electron source and the protective film.

XII. Apparatus according to one of feature combinations IX to XI,
wherein the apparatus has a cassette receptacle for receiving a cassette, wherein the cassette at least partially defines the material channel and the at least one secondary channel and contains a foil receptacle for receiving the protective foil, and the electron source is arranged movably, in particular pivotably and/or displaceably, relative to the cassette receptacle in such a way that it can be moved away from the cassette.

XIII. Apparatus according to feature combination XII, wherein a cassette is inserted in the cassette receptacle, which at least partially defines the material channel and the at least one secondary channel and contains a film receptacle by which the protective film is received.

XIV. Apparatus according to one of the preceding feature combinations,
wherein the apparatus contains a suction device for sucking off process gas surrounding the material downstream of the treatment zone.

XV. Apparatus according to one of the preceding feature combinations,
wherein the apparatus has a sorting device downstream of the treatment zone, which contains a measuring unit and an ejection unit, which are designed in such a way that individual particles of the material can be ejected by means of the ejection unit on the basis of at least one characteristic of the particles measured by means of the measuring unit.

XVI. Apparatus according to one of the preceding combinations of characteristics,
the apparatus having at least one gas outlet opening arranged downstream of the treatment zone for blowing a cleaning gas onto the material.

The terms "downstream" and "upstream" used above and below refer to the direction of material flow, i.e. the direction of flow of the particulate material when the apparatus is operated as intended. Consequently, a first unit is considered to be downstream of a second unit if the material passes through it after the second unit when the apparatus is operated as intended. Similarly, a first unit is considered to be upstream of a second unit if the material passes through it before the second unit when the apparatus is operated as intended.

In a further aspect, the invention also relates to a process for pasteurizing and/or sterilizing particulate material. This process comprises the following steps:
a) generating an electron beam,
b) pasteurizing and/or sterilizing the materials, in particular freely falling materials, by means of the electron beam in a treatment zone.

For many materials, in particular for a large number of spices, it has proved advantageous for the materials to move through the treatment zone at a velocity which is in the range from 1 m/s to 5 m/s, preferably from 2 m/s to 4 m/s, particularly preferably from 2 m/s to 3 m/s. This velocity can be adjusted, for example, by the length and angle of inclination of an upstream sliding surface, as mentioned above. The higher the velocity of the material, the greater the attainable throughput. In free fall, the velocity is independent of the throughput, so that throughputs in the range from 100 kg/h to 1000 kg/h can be achieved at the same velocity, for example. The throughput can depend on the vibration of a vibration surface(s) and the dimensions and orientations of any deflecting and sliding surface. In addition, the probability of collisions of the particles with the electron source or a protective film already mentioned above decreases with increasing velocity of the material. On the other hand, the velocities must not be too high, so that the material remains in the electron beam long enough to be pasteurized and/or sterilized.

The electrons of the electron beam preferably have an energy in the range from 80 keV to 300 keV, preferably 140 keV to 280 keV, especially preferably 180 keV to 260 keV. Lower electron energies would not produce sufficient pasteurization and/or sterilization. Higher electron energies could not achieve significantly higher degrees of pasteurization and/or sterilization.

Advantageously, the material is exposed to the electron beam for a treatment time in the range from 5 ms to 25 ms. This is because a certain minimum treatment time is required for sufficient pasteurization and/or sterilization. Too long treatment times have not shown a significantly increased degree of pasteurization and/or sterilization and would also reduce the throughput.

It is also advantageous to expose the material to a radiation dose by means of the electron beam which is in the range from 1 kGy to 45 kGy, preferably from 8 kGy to 30 kGy, particularly preferably from 10 kGy to 16 kGy.

The electron current density in the treatment zone is preferably in the range from $10^{15}$ $s^{-1} \cdot cm^{-2}$ to $2.77 \cdot 10^{15}$ $s^{-1} \cdot cm^{-2}$.

Furthermore, the process may have one or more of the features disclosed in the applicant's international patent application PCT/EP2017/070842 mentioned above:

XVII. Process for pasteurizing and/or sterilizing particulate material, in particular with an apparatus as disclosed above, comprising the following steps:
a) conveying and singulating the material by means of a preferably substantially horizontal first vibration surface which is excited to vibrations and has a plurality of channels in which the material is conveyed and by means of which it is singulated,
b generating an electron beam,
c) pasteurizing and/or sterilizing the materials, in particular freely falling materials, by means of the electron beam in a treatment zone.

XVIII. Process for pasteurizing and/or sterilizing particulate material, in particular with an apparatus as disclosed above, comprising the following steps:
b) generating an electron beam,
c) Pasteurizing and/or sterilizing the materials, in particular freely falling materials, by means of the electron beam in a treatment zone, in particular a process according to feature combination of XVII, wherein the material flows in the region of the treatment zone through a material channel in which the material is pasteurized and/or sterilized by means of the electron beam, characterized in that a fluid flows through at least one secondary channel which runs at least partially between the electron source and the material channel and is fluid-separated from the material channel.

XIX. Process according to feature combination XVIII, whereby the protective film separates the material channel from the secondary channel.

XX. Process according to one of feature combinations XVIII and XIX, wherein the secondary channel is at least partially located between the electron source and the protective film.

XXI. Process according to one of feature combinations XVII to XX, wherein the process gas surrounding the material is sucked off after the pasteurization and/or sterilization, in particular at a suction velocity which is 1 to 3 times, preferably 1 to 1.5 times the velocity of the material during the pasteurization and/or sterilization.

The materials may be food products such as cereals such as soya, breakfast cereals, snacks, nuts such as dried coconuts, almonds, peanut butter, cocoa beans, chocolate, chocolate liquid, chocolate powder, chocolate chips, cocoa products, pulses, coffee, seeds such as pumpkin seeds, spices (such as turmeric, especially in slices), tea mixtures, dried fruits, pistachios, dried protein products, bakery products, sugar, potato products, pasta, baby food, dried egg products, soya products such as soybeans, thickeners, yeasts, yeast extracts, gelatine or enzymes.

Alternatively, the material may be a pet food, such as pellets, feed for ruminants, poultry, aquatic animals (especially fish) or pets, or compound feed.

However, it is also conceivable and within the scope of the invention that the material may be a plastic such as PET, for example, in the form of flakes or pellets.

In the following, the invention is explained in more detail by means of an example and several drawings.

Figure 1:
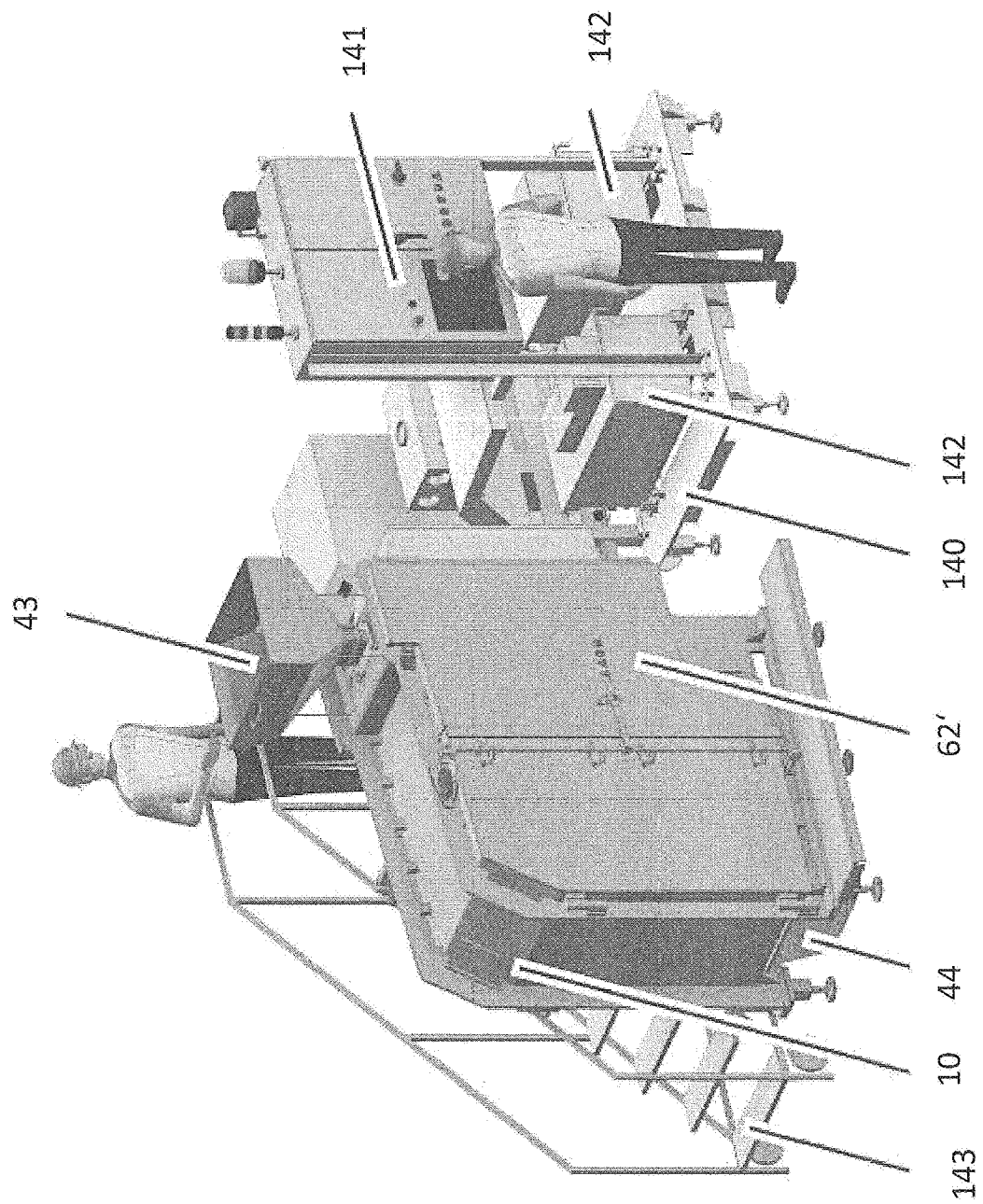
FIG. 1 shows a perspective view of an apparatus according to the invention.
Figure 2:
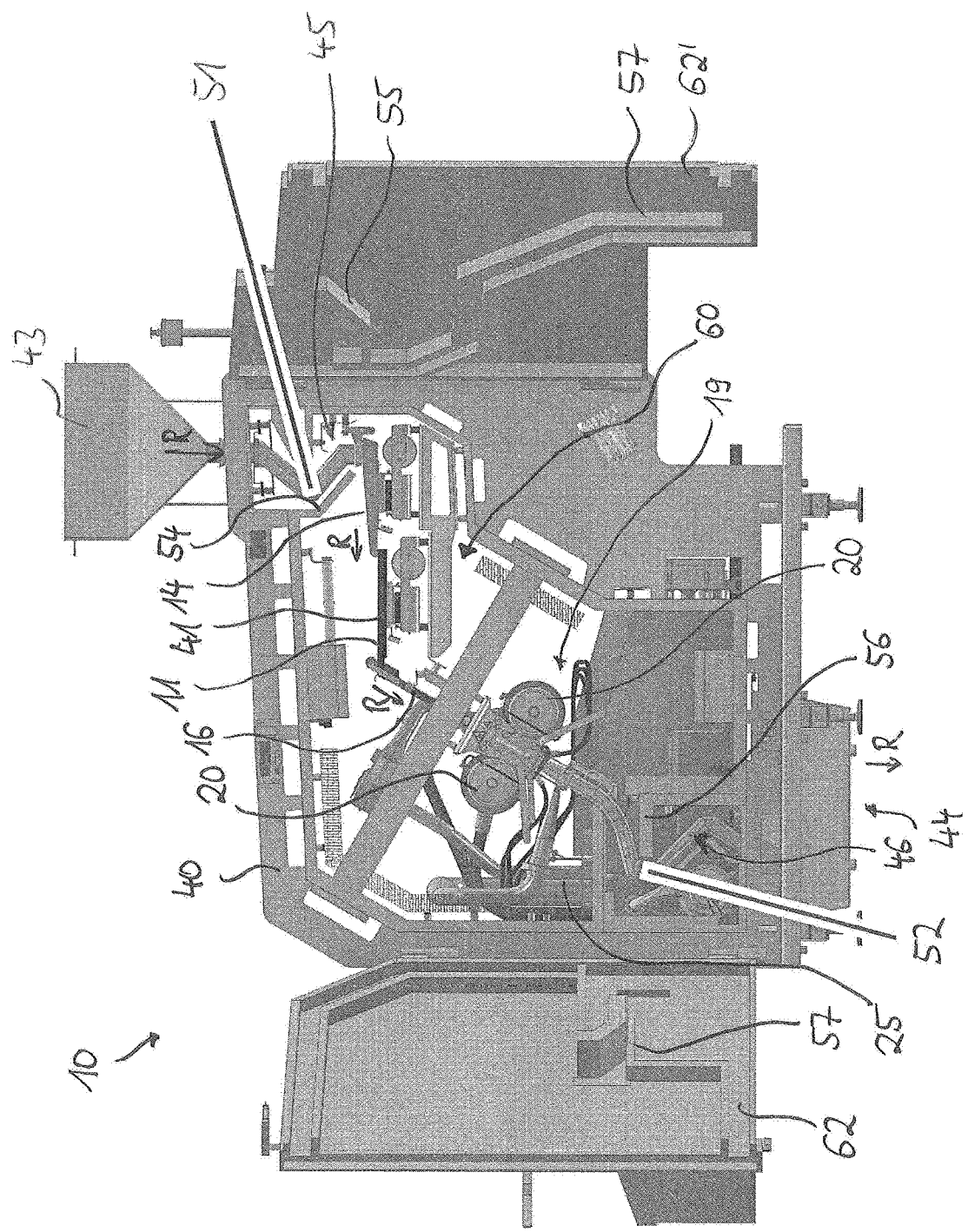
FIG. 2 shows a front view of the apparatus with the doors open.
Figure 3:
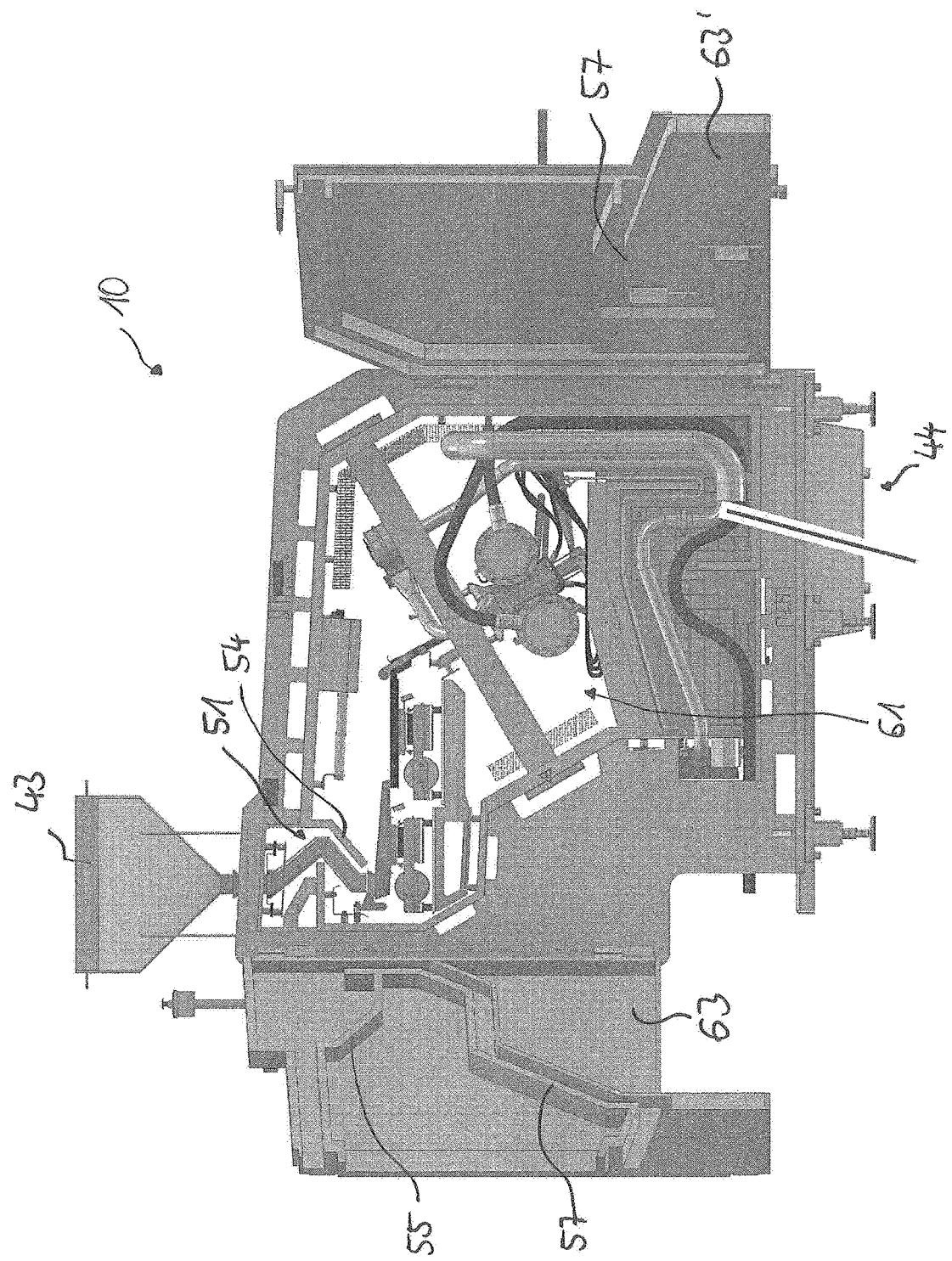
FIG. 3 shows a rear view of the apparatus with the doors open.

The apparatus 10 shown in FIGS. 1 to 3 is intended for pasteurizing and/or sterilizing particulate material, such as a spice, sesame, almonds or peeled pistachios. The apparatus 10 contains an outer housing 40, a material inlet 43, a material outlet 44 and a material guide channel 41 in which the material can be guided from the material inlet 43 along a material guide direction R through the apparatus 10 to the material outlet 44. Outside the outer housing 40 of the apparatus 10, there is an electric rack 140 with a switch cabinet 141 and two generators 142 for supplying the electron sources 20 described below and a platform 143.

As shown in FIGS. 2 and 3, the apparatus 10 also contains a dosing apparatus not shown here, with which the material can be dosed onto a first vibration surface 14 which can be excited to oscillate. With the aid of this first vibration surface 14, the throughput of the material can be controlled and a pre-singulation can already take place. Downstream of the first vibration surface 14, the apparatus 10 contains a second vibration surface 11 which can be excited into oscillations, enabling the material to be conveyed further downstream and singulated. Downstream of the vibration surface 11, there is an inclined sliding surface 16. Even further downstream, the apparatus 10 contains a treatment zone 19 where the material is pasteurized and/or sterilized in a free free-falling manner by means of an electron beam generated by two opposite electron sources 20. The apparatus 10 also contains a suction device 25 with which process gas surrounding the material can be extracted downstream of the treatment zone 19. The vibration surfaces 14 and 11 as well as the sliding surface 16 form some of the wall elements that define the material guide channel 41.

According to the present invention, the apparatus 10 has several internal shieldings 51, 52 arranged inside the outer housing 40 and enclosing the material guide channel 41 along the material guide direction R, with shielding elements 54, 55, 56, 57 which serve to shield the radiation generated during the treatment in the treatment zone 19 and which may consist of lead, for example.

The material guide channel 41 contains two channel sections 45, 46, in which the inner shieldings 51, 52 enclose it in a labyrinth-like manner, inter alia a material inlet channel 45, in which the material can be guided from the material inlet 43 to the treatment zone 19, and a material outlet channel 46, in which the material can be guided from the treatment zone 19 to the material outlet 44. The inner shielding 51 enclosing the material inlet channel 45 has shielding elements 54 and 55 and the inner shielding 52 enclosing the material outlet channel 46 has shielding elements 56 and 57, as explained in more detail below.

The outer housing 40 of the apparatus 10 has several openings, namely inter alia a front opening 60 shown in FIG. 2 and a rear opening 61 shown in FIG. 3, the front opening 60 being closable in a closed position by means of a first door 62 and a second door 62' and the rear opening 61 being closable in a closed position by means of a third door 63 and a fourth door 63'. At the inner sides 64, the doors 62, 62', 63, 63' contain the shielding elements 55 and 57. The apparatus 10 further contains static shielding elements 54 and 56. In the closed position of the doors 62, 62', 63, 63' shown in FIG. 1, the shielding elements 54, 55, 56, 57 together enclose the material guide channel 41 in a labyrinth-like manner.

For pasteurizing and/or sterilizing particulate material by means of this apparatus 10 the following steps are carried out:

By means of the first vibration surface 14, the throughput of the material is controlled and a pre-singulation takes place. On the second vibration surface 11, the material is further conveyed and singulated. An electron beam is generated by the electron sources 20. The freely falling material is then pasteurized and/or sterilized by means of the electron beam in the treatment zone 19.

In the case of spices, the material moves advantageously at a velocity of 2.5 m/s through the treatment zone 19. This velocity can be adjusted by the length and angle of inclination of the sliding surface 16. The electrons of the electron beam have an energy in the range from 80 keV to 300 keV, for example at 250 keV. In the treatment zone 19, the electron beam has a mean current density which is in the range from $10^{15}$ s$^{-1}$·cm$^{-2}$ to $2.77 \cdot 10^{15}$ s$^{-1}$·cm$^{-2}$. The material is exposed to the electron beam for a treatment time which can be in the range from 5 ms to 25 ms, for example 15 ms. the electron beam exposes the material to a radiation dose in the range from 1 kGy to 45 kGy, which may be 12 kGy for example. After pasteurization and/or sterilization in treatment zone 19, the process gas surrounding the material is extracted by means of the extraction apparatus 25 at a preferred extraction velocity of 1 to 1.5 times the velocity of the material during pasteurization and/or sterilization.

Thanks to the internal shieldings 51, 52, the risks due to the radiation generated during treatment in treatment zone 19 are reduced considerably further than would be possible with only the external housing 40. This means that the materials can also be protected from the potentially harmful radiation inside the apparatus 10, namely away from treatment zone 19. In addition, the surroundings of the apparatus 10, in particular its operator, can be protected even more effectively against possible risks of radiation. With the doors 62, 62', 63, 63' open, many of the components of the apparatus are accessible—in particular a cassette 24 located in the area of treatment zone 19, which holds two protective foils 23 made of titanium through which the electron beam passes.

The invention claimed is:

1. An apparatus for pasteurizing and/or sterilizing particulate material, the apparatus comprising:
    an outer casing,
    a material inlet,
    a material outlet,
    a material guide channel in which the material can be guided from the material inlet along a material guide direction through the apparatus to the material outlet,
    at least one electron source arranged within the housing for generating an electron beam, and
    a treatment zone arranged in the material guide channel in which the material can be pasteurized and/or sterilized by means of the electron beam,
    wherein the apparatus has at least one inner shielding arranged inside the outer housing and enclosing the material guide channel, and the inner shielding has at least one shielding element for shielding radiation produced during the treatment;
    wherein the housing has at least one opening which can be closed by at least one closure element associated therewith, and the closure element contains at least one of the shielding elements on an inner side.

2. The apparatus according to claim 1, wherein the material guiding channel has at least one channel section in which the inner shielding encloses in a labyrinth-like manner.

3. The apparatus according to claim 2, wherein the material guide channel contains a material inlet channel in which the material can be guided from the material inlet to the treatment zone, and at least one inner shielding encloses the material inlet channel in a labyrinth-like manner.

4. The apparatus according to claim 2, wherein the material guide channel contains a material outlet channel in which the material can be guided from the treatment zone to the material outlet, and at least one inner shielding encloses the material outlet channel in a labyrinth-like manner.

5. The apparatus according to claim 1, wherein at least one shielding includes a static first shielding element and the shielding element of the closure member forms a second shielding element, and the first shielding element and the second shielding element, in a closed position of the closure element in which the closure element closes the opening associated therewith, together enclose the material guide channel.

6. The apparatus according to claim 5, wherein the first shielding element and the second shielding together enclose the material guide channel in a labyrinth-like manner.

7. The apparatus according to claim 1, wherein the shielding elements have a multi-layer structure with at least one inner layer of lead and two outer layers of another material.

8. The apparatus according to claim 1, wherein the material guide channel is delimited by wall elements of which at least one is connected or movably connectable to the housing.

9. The apparatus as claimed in claim 8, wherein the at least one wall element is releasably connected or connectable to the housing.

10. The apparatus as claimed in claim 1, wherein the treatment zone is arranged such that the material can be pasteurized and/or sterilized in a free-falling manner.

11. The apparatus as claimed in claim 1, wherein the inner shielding encloses the material guide along the material guide direction.

12. A method for pasteurizing and/or sterilizing particulate material with an apparatus according to claim 1, in which the method comprises the following steps:
    a) generating an electron beam by the at least one electron source, and
    b) pasteurizing and/or sterilizing the material by the electron beam in the treatment zone.

13. The method according to claim 12, wherein the material moves through the treatment zone at a velocity which is in a range from 1 ms to 5 ms.

14. The method according to claim 12, wherein the electrons of the electron beam have an energy which is in a range from 80 keV to 300 keV.

15. The method according to claim 12, wherein the material is exposed to the electron beam for a treatment time ranging from 5 ms to 25 ms.

16. The method according to claim 12, wherein the material is exposed by the electron beam to a radiation dose which is in the range from 1 kGy to 45 kGy.

17. The method according to claim 12, wherein the electron beam in the treatment zone has an average current density which is in the range from $10^{15}$ $s^{-1}$ $cm^{-2}$ to $2.77 \cdot 10^{15}$ $s^{-1}$ $cm^{-2}$.

18. The method according to claim 12, wherein the material, in step b), is pasteurized and/or sterilized in a free-falling manner.

19. The method according to claim 12, where the material is selected from the group consisting of:
    foods,
    pet food, feed for ruminants, poultry, aquatic animals or pets, or compound feed, or
    plastic.

* * * * *